United States Patent [19]

van Wijngaarden et al.

[11] Patent Number: 5,102,901
[45] Date of Patent: Apr. 7, 1992

[54] NEW 3-N SUBSTITUTED CARBAMOYL-INDOLE DERIVATIVES

[75] Inventors: Ineke van Wijngaarden; Hans H. Haeck; Derk Hamminga; Wouter Wouters, all of Weesp, Netherlands

[73] Assignee: Duphar International Research B.V., Weesp, Netherlands

[21] Appl. No.: 508,420

[22] Filed: Apr. 13, 1990

[30] Foreign Application Priority Data

Apr. 18, 1989 [NL] Netherlands ............ 8900963

[51] Int. Cl.$^5$ ............ A61K 31/40; A61K 31/415; C07D 403/00; C07D 513/00
[52] U.S. Cl. ............ 514/397; 514/224.5; 514/294; 544/32; 546/94; 540/585; 548/336
[58] Field of Search ............ 544/32; 546/94; 540/585; 548/336; 514/397

[56] References Cited

U.S. PATENT DOCUMENTS

| | | | |
|---|---|---|---|
| 4,691,016 | 9/1987 | Stern | 546/94 |
| 4,808,581 | 2/1989 | Oxford et al. | 548/336 |
| 4,950,681 | 8/1990 | Cavalla et al. | 548/336 |
| 4,950,759 | 8/1990 | van Wijngaarden | 546/94 |
| 4,963,546 | 10/1990 | North et al. | 546/94 |

FOREIGN PATENT DOCUMENTS

| | | | |
|---|---|---|---|
| 315316 | 5/1989 | European Pat. Off. | 548/336 |
| 347229 | 12/1989 | European Pat. Off. | 548/336 |

OTHER PUBLICATIONS

Masato et al., Chem. Abst. 104-10589d (1986).
Oxford et al., Chem. Abst. 113-6338q (1990).

*Primary Examiner*—Cecilia Shen
*Attorney, Agent, or Firm*—Stevens, Davis, Miller & Mosher

[57] ABSTRACT

The invention relates to a group of new 3-N substituted carbamoyl-indole derivatives of the formula

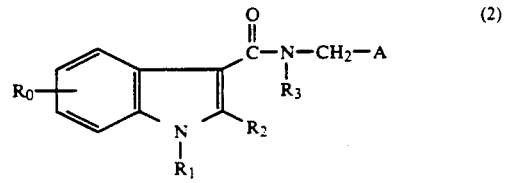

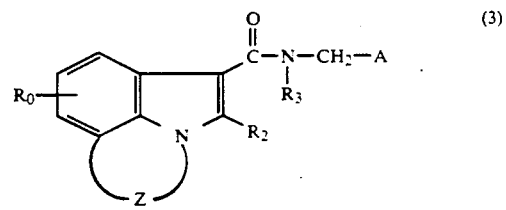

having an antagonistic activity on 5-HT receptors. The compounds can be used for the treatment of symptoms which are caused by excessive stimulation of said receptors in the gastrointestinal system, the central nervous system, the cardiovascular system, the respiratory system, and for alleviating or preventing withdrawal symptoms which are induced by abuse of drugs.

3 Claims, No Drawings

NEW 3-N SUBSTITUTED CARBAMOYL-INDOLE DERIVATIVES

The invention relates to new heterocyclic compounds having an antagonistic activity on 5-hydroxytryptamine (5-HT) receptors, to the preparation thereof and to pharmaceutical compositions comprising such a new compound as an active substance.

British Patent Specification no. 2153821 relates to heterocyclic compounds having an antagonistic activity on 5-HT receptors. These known compounds have the general formula 1

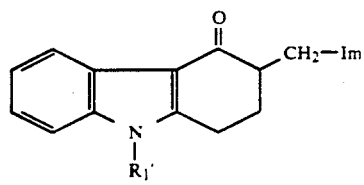

wherein $R_1'$ is hydrogen, alkyl, alkenyl, cycloalkyl, cycloalkylalkyl, phenylalkyl, and Im is an optionally substituted imidazole radical.

It has been found surprisingly that compounds of formulae 2 and 3

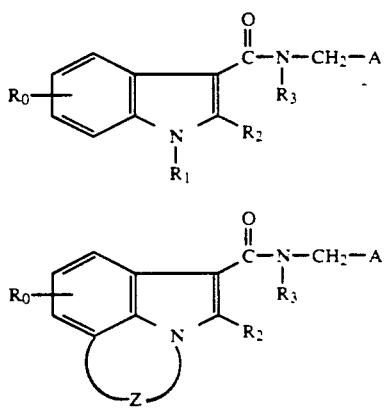

wherein
- $R_0$ is hydrogen, alkyl or alkoxy having 1–4 C-atoms, hydroxy, halogen, trifluormethyl, a group $R_6R_7N$ or $R_6R_7$-N-CO, wherein $R_6$ and $R_7$ are hydrogen or alkyl having 1–4 C-atoms or wherein $R_6R_7N$ is a saturated 5- or 6 membered ring,
- $R_2$ and $R_3$ independently of each other are a hydrogen atom, a branched or non-branched alkyl group having 1–4 C-atoms, alkenyl group having 3–6 C-atoms, cycloalkyl group or benzyl,
- $R_1$ is hydrogen, 1–8 C alkyl, 3–7 C cycloalkyl, 3–7 C cycloalkyl-(1–4 C)alkyl, 3–6 C alkenyl, 3–8 C alkynyl, phenyl or phenyl-(1–3 C)alkyl, wherein the phenyl group may be substituted, or $R_1$ is a group $COOR_8$, $COR_8$, $SO_2R_8$, wherein $R_8$ is 1–4 C alkyl, 3–7 C cycloalkyl, phenyl or phenyl-(1–2 C)alkyl, or $R_1$ is a group

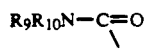

wherein $R_9$ and $R_{10}$ independently of each other are hydrogen, 1–4 C alkyl, 3–7 C cycloakyl, phenyl or phenyl-(1–2 C)alkyl, or wherein $R_9$ and $R_{10}$ together with the nitrogen atom to which they are bound constitute a saturated 5- or 6 membered ring,
- Z together with the carbon atom and the nitrogen atom and the intermediate carbon atom forms a heterocyclic group which consists of 5–8 ring atoms and wherein besides the nitrogen atom already present, a second hetero atom from the group N, O or S may be present, which ring may be substituted with 1–4 alkyl groups having 1–4 C-atoms, or which ring may be annelated with a saturated or non-saturated carbocyclic or heterocyclic ring, which consists of 5- or 6-ring atoms and which may be substituted,
- A is a group of formula 4 and 5

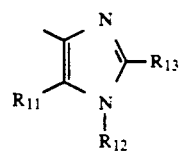

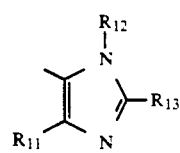

wherein one of the groups $R_{11}$, $R_{12}$ and $R_{13}$ is hydrogen, alkyl having 1–6 C-atoms, cycloalkyl having 3–7 C-atoms, alkenyl having 2–6 C-atoms, and the two other groups independently of each other are hydrogen or alkyl having 1–4 C-atoms, and the pharmaceutically acceptable acid addition salts thereof have a similar but considerable prolonged activity and a lower toxicity than the known compounds of formula 1.

Suitable acids with which the compounds of formulae 2 and 3 according to the invention can form pharmaceutically acceptable acid addition salts are, for example, hydrochloric acid, sulphuric acid, phosphoric acid, nitric acid, and organic acids, for example, citric acid, fumaric acid, maleic acid, tartaric acid, acetic acid, benzoic acid, p-toluenesulphonic acid, methanesulphonic acid and the like.

In the case in which the ring Z is substituted and/or annelated, one or more chiral centres may be present. Both the racemates and the individual enantiomers of compounds of formulae 2 and 3 belong to the invention.

The antagonistic activity of the compounds of formulae 2 and 3 on the 5-HT-induced response was determined and measured in the von Bezold-Jarisch reflex test in rats. The affinity to "neuronal" 5-HT receptors was determined and measured by the displacement of ($^3$H)GR 38032 F of neuroblastoma cells.

On the basis of the antagonistic activity on this type of 5-HT receptors the compounds may be used for the treatment of symptoms which are caused by overstimulation of the said receptors a) in the gastrointestinal system (nausea and vomitting as a result of exogenous factors, for example, cancer therapy, or endogenous factors, for example, stasis of the stomach and migraine), ulcer, dyspepsia, spasms, irritable bowel syndrome, etc., or b) in the central nervous system (hallucinations, delusions, manias, anxiety, depression, pain, improvement of the vigility, etc.) or c) in the cardiovascular system, for example, spasms of the vessels, arrhythmia, etc., or d) in the respiratory system (including nasal disturbances and disturbances of bronchi and lungs) or e) for relieving withdrawal symptoms which are induced by abuse of drugs.

The compounds according to the invention and their salts can be brought into forms suitable for administration, for example, pills, tablets, coated tablets, capsules, powders, injection liquids and the like by means of techniques conventionally used for this purpose and while using suitable auxiliary substances, for example, solid or liquid carrier materials.

The dosage in which the compounds according to the invention may be used depend on the severity and the nature of the disease to be treated and on the way of administration. As a rule the dosage will be between 0.05 and 20 mg, preferably between 0.1 and 10 mg of active substance daily.

The compounds of formulae 2 and 3, wherein $R_0$, $R_1$, $R_2$, $R_3$, Z and A have the meanings mentioned hereinbefore may be prepared in at least one of the following manners:

i) by reaction of a compound of formula 6 and 7

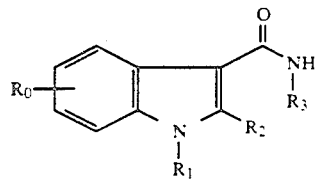

(6)

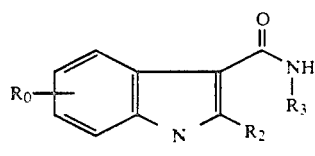

(7)

wherein $R_0$, $R_1$, $R_2$, $R_3$, and Z have the above-mentioned meanings, with a compound of formula 8

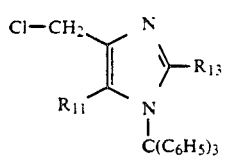

(8)

wherein $R_{11}$ and $R_{13}$ have the meanings mentioned in formulae 4 and 5, in the presence of potassium hydroxide, preferably in a solvent, for example, dimethylsulphoxide, dimethyl formamide, etc., succeeded by splitting off the triphenyl methyl group.

The starting compounds of formulae 6 and 7 required for these reactions may be prepared:

a) from the corresponding compounds of formulae 9 and 10

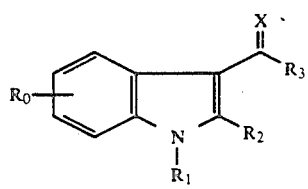

(9)

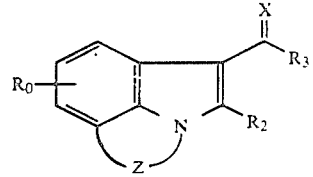

(10)

wherein X is the group =NOH, by means of the Beckmann reaction, or b) from the corresponding compounds of formulae 9 and 10, wherein X is oxygen, by means of the Schmidt reaction.

The compounds of formulae 9 and 10, wherein X is the group =NOH, can be prepared in a manner known per se from the analogous compounds of formulae 9 and 10, wherein X is an oxygen atom. The compounds wherein X is oxygen are known compounds or may be prepared in a manner known for analogous compounds.

c) by reaction of a compound of formula 11 and 12

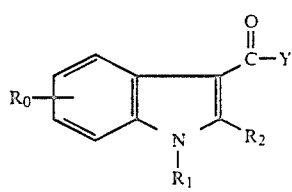

(11)

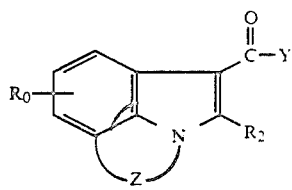

(12)

wherein $R_0$, $R_1$, $R_2$ and Z have the meanings mentioned in formulae 2 and 3 and Y is a group which may be replaced by a nucleophile, for example, an alkoxy group, a halogen atom or a group of formula 13

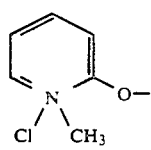

(13)

with a compound of the formulae $R_3$—$NH_2$.

The starting compounds of formulae 11 and 12 required for this purpose are known compounds or may be prepared analogously to known compounds. (see EP 0322016)

ii) by metalation of a compound of formula 2 and 3, wherein $R_0$, $R_1$, $R_2$, $R_3$, A and Z have the above-mentioned meanings, with the proviso that $R_1$ and/or $R_{12}$ in formula 2 or $R_{12}$ in formula 3 are a hydrogen atom, and subsequent reaction of the formed metal compound with a compound having formula $R_1$-Y or $R_{12}$-Y, wherein Y is a group which may be replaced by a nucleophile, for example, a halogen atom. The reaction is preferably carried out in a solvent, for example, dimethylsulphoxide with metalation reagents, for example, sodium hydride, potassium tertiary butoxide, etc.

The starting compounds of formulae 2 and 3 required for the said metalation may be obtained, for example, by means of the method described hereinbefore sub i), or by means of the below described methods iii) and iv).

iii) by Fischer-indole ring closure of a compound of formula 14 or 15

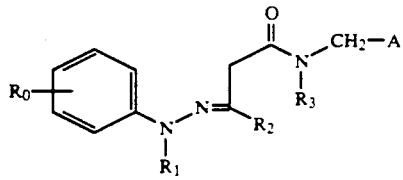

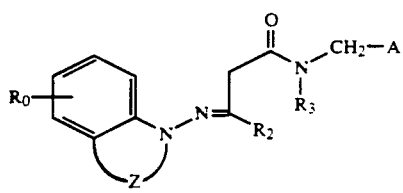

wherein $R_0$, $R_1$, $R_2$, $R_3$, A and Z have the meanings mentioned in formulae 2 and 3.

iv) by reaction of a compound of formula 11 or 12 wherein $R_0$, $R_1$, $R_2$, Y and Z have the above mentioned meanings, with a compound of formula 16

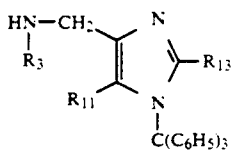

preferably in an organic solvent, for example, methylene chloride or acetonitrile whether or not in the presence of a base, for example, pyridine or triethyl amine, at temperatures between 0° and 120° C., and then splitting off the trityl group from the formed intermediate product.

The invention will now be elucidated in greater detail with reference to the following examples

EXAMPLE I

N-methyl, N-[(5-methyl-1H-imidazol-4-yl)methyl]-4-methyl-5,6-dihydro-4H-pyrrolo[3,2,1-ij]quinoline-1-carboxamide.HCl A mixture of 3.4 g (9.3 mmol) of 5-methyl-4-(methylamino) methyl-1-triphenylmethyl-1H-imidazole, 2.0 g (9.3 mmol) of 4-methyl-5,6-dihydro-4H-pyrrolo[3,2,1-ij]quinoline-1-carboxylic acid, and 2.06 g (10 mmol) of N,N-dicyclohexylcarbodiimide in 100 ml of acetonitrile was stirred for 12 hours under nitrogen. The precipitate was sucked off and the filtrate was evaporated in vacuo. The residue was dissolved in ethylacetate and washed with 2 N sodium hydroxide and saturated saline respectively, and then evaporated in vacuo. The residue was chromatographed on silicagel using methylene chloride/methanol (95/5) as an eluent. After evaporating the desired fractions 3.6 g of N-methyl, N-[(5-methyl-1-triphenylmethyl-1H-imidazol-4-yl)methyl]-4-methyl-5,6-dihydro-4H-pyrrolo[3,2,1-ij]quinoline-1-carboxamide were obtained.

3.2 g (5.67 mmol) of the obtained product was boiled for 30 minutes in a mixture of 33 ml of acetic acid and 33 ml of water, while stirring. The mixture was cooled and diluted with ice-water and sodium hydroxide until weakly alkaline. The mixture was shaken with ethyl acetate. The obtained solution was washed with saline and evaporated in vacuo. The residue was chromatographed on silicagel using methylene chloride/methanol/ammonia(93/7/0.3) as an eluent. The desired fractions were evaporated in vacuo, the residue was dissolved in ethyl acetate and alcoholic hydrochloric acid was added. The solid material was sucked off and dried. 1.0 g of the desired product were obtained.

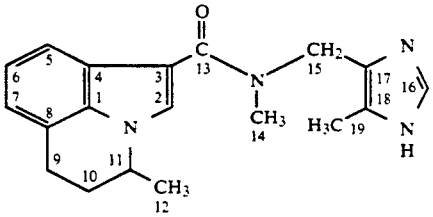

C-13 nmr (SLV: CDCl₃, ADT: triethylamine, Ref: TMS)

| 1 | 133.80 | S | 8  | 122.22 | S | 15 | 43.70  |   |
|---|--------|---|----|--------|---|----|--------|---|
| 2 | 127.48 | D | 9  | 23.30  | T | 16 | 133.55 | D |
| 3 | 109.97 | S | 10 | 30.50  | T | 17 | 128.70 |   |
| 4 | 124.64 | S | 11 | 50.12  | D | 18 | 127.48 |   |
| 5 | 119.42 | D | 12 | 20.48  | Q | 19 | 10.45  | Q |
| 6 | 121.20 | D | 13 | 168.28 | S |    |        |   |
| 7 | 118.32 | D | 14 | 35.90  |   |    |        |   |

BROAD LINES FOR CARBONS 14 TO 19

In the same manner were obtained:
N-Methyl,N-[(5-methyl-1H-imidazol-4-yl)methyl]-2-methyl-5,6-dihydro-4H-pyrrolo[3,2,1-ij]quinoline-1-carboxamide hydrochloride

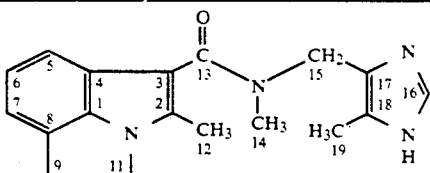

C-13-NMR (SLV: CDCl₃, ADT: Triethylamine, Ref: TMS)

| 1 | 133.30 | S | 8  | 121.68 | S | 15 | *.00   |   |
|---|--------|---|----|--------|---|----|--------|---|
| 2 | 138.16 | S | 9  | 24.56  | T | 16 | 133.17 | D |
| 3 | 107.17 | S | 10 | 22.70  | T | 17 | 130.20 |   |
| 4 | 123.69 | S | 11 | 41.69  | T | 18 | 125.90 |   |
| 5 | 116.81 | D | 12 | 11.03  | Q | 19 | 10.55  |   |
| 6 | 118.65 | D | 13 | 169.45 | S |    |        |   |
| 7 | 120.77 | D | 14 | 36.60  |   |    |        |   |

LINES OF C-ATOMS 14 15 17 18 AND 19 ARE BROAD
C.S. OF C-ATOM 15 IS ABOUT 42 PPM

2) N-Methyl,N-[(5-methyl-1H-imidazol-4-yl)methyl]-2,3-dihydro-pyrrolo[1,2,3-de][1,4]benzothiazine-6-carboxamide

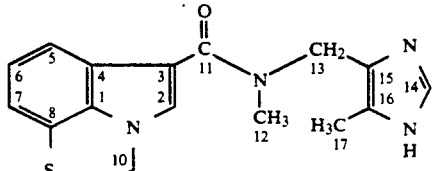

C-13-NMR (SLV: CDCl₃, Ref: TMS)

| 1 | 130.14 | S | 7 | 121.85 | D # | 13 | 43.20 |

C-13-NMR (SLV: CDCl₃, Ref: TMS)

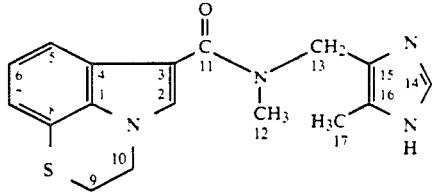

| | | | | | | | | | |
|---|---|---|---|---|---|---|---|---|---|
| 2 | 129.67 | D | 8 | 117.26 | S | 14 | 133.85 | D |
| 3 | 110.18 | S | 9 | 26.01 | T | 15 | *.00 | |
| 4 | 125.48 | S | 10 | 45.99 | T | 16 | *.00 | |
| 5 | 117.91 | D # | 11 | 167.63 | S | 17 | 10.70 | |
| 6 | 119.26 | D # | 12 | 36.20 | | | | |

BROAD LINES FOR CARBONS 11 TO 17

3) N-Methyl, N-[(5-methyl-1H-imidazol-4-yl)methyl]-6,7-dihydro-1-methyl-indolo[1,7a,7-ab][1]benzazepine-2-carboxamide

C-13-NMR (SLV: CDCl₃, Ref: TMS)

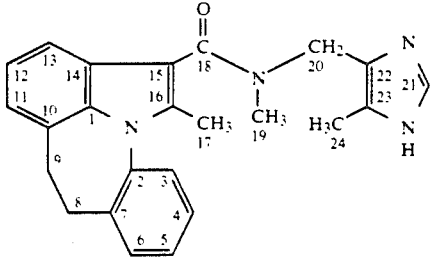

| | | | | | | | | | |
|---|---|---|---|---|---|---|---|---|---|
| 1 | 135.57 | S | 9 | 33.95 | T | 17 | 13.95 | Q |
| 2 | 137.80 | S | 10 | 126.65 | | 18 | 169.40 | |
| 3 | 125.67 | D | 11 | 126.19 | D | 19 | 36.67 | |
| 4 | 126.36 | D | 12 | 120.92 | D | 20 | 41.56 | |
| 5 | 116.90 | D | 13 | 123.38 | D | 21 | 133.88 | |
| 6 | 129.88 | D | 14 | 126.94 | S | 22 | *.00 | |
| 7 | 137.66 | S | 15 | 113.90 | | 23 | *.00 | |
| 8 | 34.38 | T | 16 | *.00 | | 24 | 12.10 | |

CARBONS 15 18 19 20 21 AND 24 ARE VERY BROAD
CARBONS 16 22 AND 23 ARE NOT SHOWN

4) N-Methyl,N-[(5-methyl-1H-imidazol-4-yl)methyl]-6,7-dihydro-indolo[1,7a,7-ab][1]benzazepine-2-carboxamide hydrochloride

C-13-NMR (SLV: CDCl₃, ADT: Triethylamine, Ref: TMS)

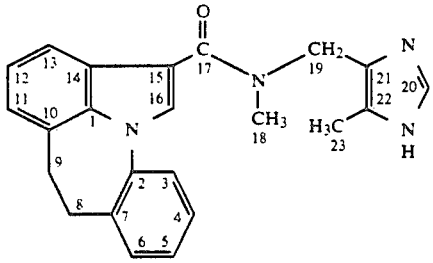

| | | | | | | | | | |
|---|---|---|---|---|---|---|---|---|---|
| 1 | 134.50 | S | 9 | 34.20 | T | 17 | 167.42 | S |
| 2 | 139.49 | S | 10 | 127.65 | S | 18 | *.00 | |
| 3 | 125.53 | D | 11 | 121.19 | D | 19 | *.00 | |
| 4 | 127.56 | D | 12 | 118.92 | D | 20 | 133.89 | D |
| 5 | 123.74 | D | 13 | 122.42 | D | 21 | *.00 | |
| 6 | 130.61 | D | 14 | 128.32 | S | 22 | *.00 | |
| 7 | 134.97 | S | 15 | 113.48 | S | 23 | 10.42 | |
| 8 | 34.74 | T | 16 | 128.98 | D | | | |

CARBONS 14 16 AND 20 ARE BROAD
18 19 21 AND 22 ARE NOT VISIBLE

5) N-Methyl,N-[(5-methyl-1H-imidazol-4-yl)methyl[-4,5,6,7,-tetrahydro-pyrrolo[3,2,1-jk][1]benzazepine-1-carboxamide

C-13-NMR (SLV: CDCl₃, Ref: TMS, ADT TEA)

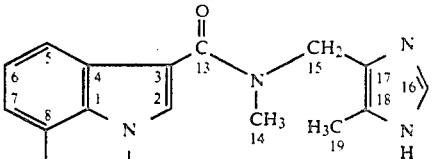

| | | | | | | | | | |
|---|---|---|---|---|---|---|---|---|---|
| 1 | 136.34 | S | 8 | 127.28 | S | 15 | 43.27 | |
| 2 | 131.99 | D | 9 | 28.54 | T | 16 | 133.44 | D |
| 3 | 109.71 | S | 10 | 27.04 | T | 17 | 127.81 | |
| 4 | 128.15 | S | 11 | 33.07 | T | 18 | 127.54 | |
| 5 | 118.64 | D | 12 | 50.06 | T | 19 | 10.07 | Q |
| 6 | 122.81 | D | 13 | 167.77 | S | | | |
| 7 | 120.96 | D | 14 | 35.55 | | | | |

LINES OF C-ATOMS 14 15 17 AND 18 ARE VERY BROAD

EXAMPLE II

N-methyl, N-[(5-methyl-1H-imidazol-4-yl)methyl]-5,6-dihydro4H-pyrrolo[3,2,1-ij]quinoline-1carboxamide 1.2 g (6.0 mmol) of 5,6-dihydro-4H-pyrrolo[3,2,1-ij]quinoline-1-carboxylic acid were mixed with 15 ml of thionyl chloride and boiled for 2.5 hours. The excess of thionyl chloride was distilled off in vacuo, and toluene was added. The mixture was evaporated in vacuo again, and the residue was dissolved in 20 ml of acetonitrile. A solution of 2.2 g (6.0 mmol) of 5-methyl-4-(methylamino)methyl-1-triphenylmethyl-1H-imidazole and 1.7 ml (12 mmol) of triethyl amine in 25 ml of acetonitrile was added, the mixture was boiled for 1 hour, and evaporated in vacuo. The residue was shaken with methylene chloride and 2 N NaOH. The organic layer was washed with water and evaporated in vacuo. The residue was chromatographed on silicagel using methylene chloride/methanol (95/5) as an eluent. After evaporating the desired fractions 2.0 g of N-methyl, N-[(5-methyl-1-triphenylmethyl-1H-imidazol-4-yl)methyl]-5,6-dihydro-4H-pyrrolo [3,2,1-ij]quinoline-1-carboxamide were obtained. This product was treated as described in Example I to remove the triphenylmethyl group, and purified. 0.46 g of the desired title compound were obtained.

C-13-NMR (SLV: CDCl₃, Ref: TMS):

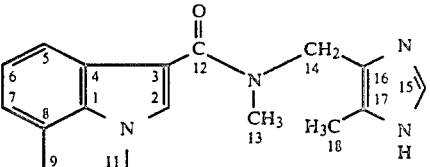

| | | | | | | | | | |
|---|---|---|---|---|---|---|---|---|---|
| 1 | 133.92 | S | 7 | 121.53 | D | 13 | 36.68 | |
| 2 | 129.34 | D | 8 | 122.28 | S | 14 | 43.09 | |
| 3 | 109.92 | S | 9 | 24.50 | T | 15 | 133.78 | D |
| 4 | 124.37 | S | 10 | 22.76 | T | 16 | *.00 | |
| 5 | 118.59 | D | 11 | 44.55 | T | 17 | 125.00 | |
| 6 | 119.60 | D | 12 | 168.73 | S | 18 | 11.47 | Q |

LINES OF C-ATOMS 13 14 16 17 AND 18 ARE BROAD
C.S. OF C-ATOM 16 = CA. 132 PPM

In the same manner the following compounds were obtained:

1. N-[(5-methyl-1H-imidazol-4-yl)methyl-5,6-dihydro-4H-pyrrolo[3,2,1-ij]quinoline-1-carboxamide; melting point 240° C. (decomposition)

2. N-[(5-methyl-1H-imidazol-4-yl)methyl--1-methyl-indole-3-carboxamide; melting point 214°-219° C.

3. N-methyl,N-[5-methyl-1H-imidazol-4-yl)methyl-1-methylindole-3-carboxamide

---

C-13-NMR (SLV: CDCl$_3$, Additive: CH$_3$OH, Ref: TMS)

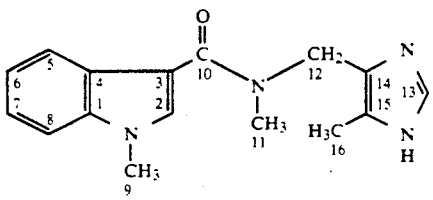

| 1 | 136.60 | S   | 7  | 122.75 | D # | 13 | 133.65 | D+ |
| 2 | 131.94 | D-  | 8  | 109.86 | D   | 14 | 129.80 |    |
| 3 | 109.25 | S   | 9  | 33.20  | Q   | 15 | 125.60 |    |
| 4 | 126.60 | D   | 10 | 168.47 | S   | 16 | 10.35  | Q  |
| 5 | 121.24 | D # | 11 | 36.80  |     |    |        |    |
| 6 | 121.01 | D # | 12 | 42.80  |     |    |        |    |

MOST LINES ARE BROAD

We claim:

1. A carbamoyl indole compound of formula 2

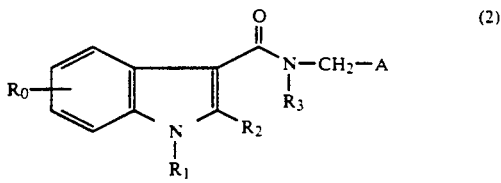

wherein
- R$_o$ is hydrogen,
- R$_2$ and R$_3$ independently of each other are hydrogen or an alkyl group having 1-2 C-atoms,
- R$_1$ is hydrogen or 1-3 C alkyl,
A is a group of formula 4 or 5 wherein R$_{11}$, R$_{12}$ and R$_{13}$ independently of each other are hydrogen or alkyl having 1-2 C-atoms, or a pharmaceutically acceptable acid addition salt thereof.

2. A pharmaceutical composition having an antigonistic activity on 5-hydroxytryptamine (5-HT) receptors which comprises as the active substance an effective component of a carbamoyl-indole compound, characterized in that it comprises at least one compound as claimed in claim 1 as an active substance.

3. A method of treating symptoms which are caused by overstimulation of 5-hydroxytryptamine receptors, characterised in that a compound as claimed in claim 1 is used.

* * * * *